United States Patent [19]

Soderkvist et al.

[11] 4,021,118

[45] May 3, 1977

[54] METHOD IN A MICROTOME FOR APPROACHING THE KNIFE TO THE SPECIMEN

[75] Inventors: Anton Soderkvist, Vallingby; Hans Lycke, Bromma, both of Sweden

[73] Assignee: LKB-Produkter AB, Bromma, Sweden

[22] Filed: Mar. 29, 1976

[21] Appl. No.: 671,370

[30] Foreign Application Priority Data

Apr. 10, 1975 Sweden .............................. 7504111

[52] U.S. Cl. .............................................. 356/156
[51] Int. Cl.² .......................................... G01N 1/06
[58] Field of Search ..................... 356/156; 350/81

[56] References Cited

FOREIGN PATENTS OR APPLICATIONS 2,434,331 12/1975 Germany ............................. 350/81
783,524 9/1957 United Kingdom ............... 356/156

Primary Examiner—John K. Corbin
Assistant Examiner—Richard A. Rosenberger
Attorney, Agent, or Firm—George H. Mitchell, Jr.

[57] ABSTRACT

A method for adjusting the position of the transparent triangular knife of a microtome with respect to a sample to be sectioned, consists of projecting a beam of light into the interior of the knife from below whereby an area of the sample above the knife edge will be illuminated by refraction of the projected beam from the upper sloping surface of the knife, the darkened area of the sample between the knife edge and the illuminated area constituting a measurement of the horizontal distance between the sample and the knife.

3 Claims, 1 Drawing Figure

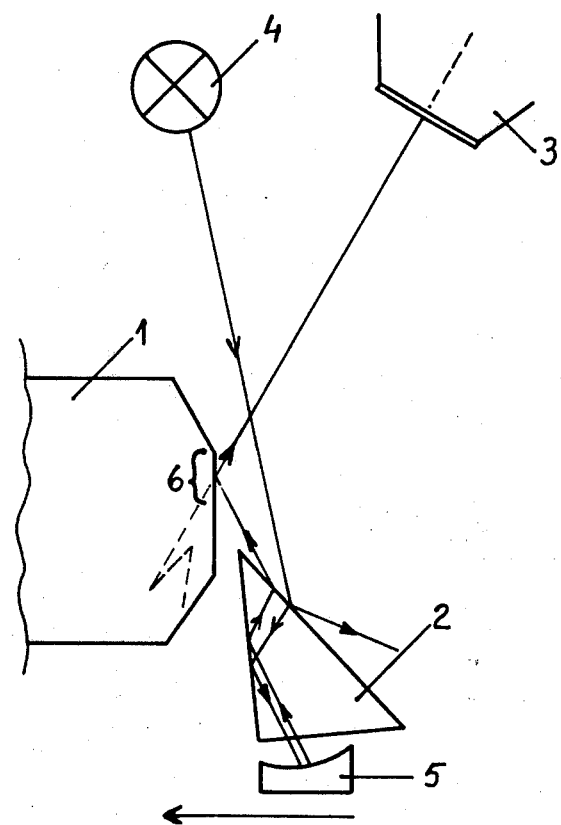

METHOD IN A MICROTOME FOR APPROACHING THE KNIFE TO THE SPECIMEN

The present invention refers to a method in a microtome where glass knife is used to cut off sections from a specimen by means of making the specimen pass the knife, the method being used for bringing the knife close to the sample before the cutting process is initiated.

Within microtomy, especially ultramicrotomy, there is a requirement of monitoring and controlling the approach of the cutting knife to the specimen surface from which sections are to be cut off. According to methods known per se this is made by having the knife and the sample lit up from below with a separate lamp located in the knife-holder under the specimen and knife. The distance between the knife and the specimen will thereby be observed as a lit up slit when viewed from above. However, especially if the area of the specimen is small the light flow will have a tendency to dazzle the opertor thus making it difficult to estimate the distance between the knife edge and the specimen when this distance is small. Light from the lamp will also pass through the specimen behind its surface which decreases the contrasts and thus the possiblity to estimate the distance of the knife from the specimen surface. Furthermore a disadvantage will appear when the slit is very narrow (about 1 micrometer) since light passing such narrow areas will give rise to so called fringes which make it difficult to estimate the width of the slit.

It is an object of the present invention to provide a method by means of which it is possible to make a safe indication of the distance from the knife edge to the surface of the specimen. The characteristics of the invention will appear from the claims enclosed to the specification.

The invention will now be described in detail reference being made to the enclosed drawing which schematically shows the light path obtained when carrying out the method according to the invention.

In the drawing reference 1 denotes a specimen block from the vertical surface of which sections are to be cut off with a glass knife 2 by means of moving the specimen block downwards against the knife edge. The knife and the specimen block are viewed from a microscope 3 and furthermore the upper surface of the knife is lit by a lamp 4. Under the knife a preferably concave mirror 5 is located. Light from the lamp will meet the upper surface of the knife. That part of the light that is not reflected in this surface passes through the knife and leaves the knife through its bottom surface whereby it is reflected in the mirror which is arranged with respect to the lamp in such a way that light reflected in the mirror after passing back through the knife will be reflected in the specimen surface. Thus a reflected image of the upper surface of the knife will be obtained on the specimen surface as has been indicated with the dotted line in the figure and the upper part 6 of the specimen surface will be lit up when viewed from the microscope. The lower edge of this lit up surface will thereby be constituted by a ling along which the knife edge is reflected in the specimen surface. When the reflected light leaves the upper surface of the knife a certain amount of diffusion will be obtained which means that light beams will pass directly from the knife surface into the microscope whereby the knife surface will give a lit up impression when viewed in the microscope. As appears from the above the image obtained in the microscope will consist of an upper lit up area 6, an intermediate dark area and a lower lit up area whereby the width of the dark area will decrease when the knife is approached to the specimen surface. One will thus obtain a dark indicating field which among other things implies that the above mentioned problem with the so called fringes is eliminated. As concerns the mirror 5 this mirror is suitably concave so that it will not be necessary to move the mirror when the knife is turned around an axis perpendicular to the plane of the drawing.

We claim:

1. A method in a microtome where a glass knife is used to cut off sections from a sample by means of making the sample pass the knife, the method being used for bringing the knife close to the sample before the cutting process is initiated, characterized in, that the surface of the knife remote from the specimen is lit up from below whereby the lit up surface of the knife will generate a reflected image in the upper part of the surface of the specimen close to the knife, whereas below this image a dark area is obtained the width of this dark area constituting a measure of the distance between the knife edge and the specimen surface.

2. Method according to claim 1, characterized in, that the knife is lit up from below by means of a mirror reflecting light incident on the upper surface of the knife.

3. Method according to claim 2, characterized in, that said mirror is concave.

* * * * *